United States Patent [19]

Conrad et al.

[11] 4,435,315

[45] Mar. 6, 1984

[54] USE OF ALKYL-SUBSTITUTED 1,3-DIOXOLANES AS PERFUMING AGENTS

[75] Inventors: Jens Conrad, Hilden; Ulf-Armin Schaper, Düsseldorf; Klaus Bruns, Krefeld-Traar, all of Fed. Rep. of Germany

[73] Assignee: Henkel Kommanditgesellschaft auf Atkien, Düsseldorf-Holthausen, Fed. Rep. of Germany

[21] Appl. No.: 366,374

[22] Filed: Apr. 7, 1982

Related U.S. Application Data

[63] Continuation of Ser. No. 226,201, Jan. 19, 1981, abandoned.

[30] Foreign Application Priority Data

Feb. 8, 1980 [DE] Fed. Rep. of Germany ....... 3004661

[51] Int. Cl.$^3$ .................................................. C11B 9/00
[52] U.S. Cl. ................... 252/522 R; 252/8.6; 252/8.9; 252/174.11; 424/49; 424/69; 424/76
[58] Field of Search ............... 252/522 R, 8.6, 8.9, 252/174.11; 424/49, 69, 76

[56] References Cited

U.S. PATENT DOCUMENTS 3,658,849 4/1972 Leffingwell ................. 252/522 R X
3,769,303 10/1973 Easter, Jr. et al. ......... 252/522 R X
3,805,804 4/1974 Quinn ................................... 131/144
3,883,558 5/1975 Lamparsky ...................... 260/340.9
4,159,347 6/1979 Yoshida et al. ......................... 426/3

FOREIGN PATENT DOCUMENTS 2147091 3/1973 France .
2225102 11/1974 France .

OTHER PUBLICATIONS

Arctander, *Perfume and Flavor Chemicals*, vol. I, Monograph No. 1402, (1969).
Hanzlik et al., *J. Org. Chem.*, vol. 43, 438, (1978).
Rosenthal et al., *J. Org. Chem.*, vol. 33, 805, (1968).
Lalende et al., *Tetrahedron Letters*, 1969, 745.
Raucher, *Tetrahedron Letters*, 1976, 1161.
Nakada, *Agric. Biol. Chem.*, vol. 41, 1761, (1977).
Tobler, *Helv. Chim. Acta.*, vol. 52, 408, (1969).

*Primary Examiner*—Thomas A. Waltz
*Attorney, Agent, or Firm*—Hammond & Littell, Weissenberger & Dippert

[57] ABSTRACT

The invention is directed to a perfumery composition consisting essentially of at least one alkyl-substituted 1,3-dioxolane and customary constituents and to the use of such a perfumery composition to impart a pleasant odor to a product.

29 Claims, No Drawings

USE OF ALKYL-SUBSTITUTED 1,3-DIOXOLANES AS PERFUMING AGENTS

This is a continuation of co-pending U.S. patent application Ser. No. 226,201, filed Jan. 19, 1981, now abandoned.

FIELD OF THE INVENTION

This invention is directed to novel perfuming agents. More particularly, this invention is directed to the use of alkyl-substituted 1,3-dioxolanes as perfuming agents as well as perfuming compositions containing such compounds.

OBJECTS OF THE INVENTION

It is an object of the invention to provide for the use of alkyl-substituted 1,3-dioxolanes as perfuming agents.

It is also an object of the invention to provide perfuming compositions based upon alkyl-substituted 1,3-dioxolanes.

These and other objects of the invention will become more apparent in the discussion below.

DETAILED DESCRIPTION OF THE INVENTION

It has been found that alkyl-substituted 1,3-dioxolanes of the general formula

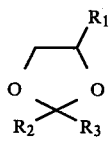
(I)

wherein $R_1$ represents alkyl of from 4 to 12 carbon atoms; $R_2$ represents hydrogen, an alkyl of from 1 to 7 carbon atoms, a cycloalkyl or cycloalkenyl of from 5 to 8 carbon atoms, or an optionally alkyl-substituted aryl; and $R_3$ represents hydrogen or an alkyl of from 1 to 3 carbon atoms, can be used in an advantageous manner as perfumes or perfuming agents with a vigorous, mainly fruity note. At least one of the alkyl-substituted 1,3-dioxolanes is used as a perfuming agent in a perfume composition.

The $R_1$ group of the compounds of Formula I can be, for example, a butyl, hexyl, octyl, decyl, or dodecyl group, and the $R_3$ group can be hydrogen or a methyl, ethyl, propyl, or isopropyl group. $R_2$ is preferably hydrogen or a methyl, ethyl, propyl, isopropyl, butyl, isobutyl, pentyl, neopentyl, hexyl, heptyl, cyclohexyl, cyclohexenyl, or cyclooctyl group. $R_2$ can also be a phenyl, lower alkyl-substituted phenyl such as toluyl or ethylphenyl, naphthyl or lower alkyl substituted naphthyl, or furyl group.

The alkyl-substituted 1,3-dioxolanes to be used as perfuming agents according to the invention are prepared by a basic, known method of organic synthesis. One course of synthesis consists of the acetalization of carbonyl compounds having the radicals $R_2$ and $R_3$ with 1,2-alkane diols having a chain length of $C_6$–$C_{14}$, in the presence of acid catalysts, while the water of reaction is removed with a solvent by azeotropic distillation or by conversion of the water of reaction with a triester of orthoformic acid. The reaction proceeds according to the following scheme:

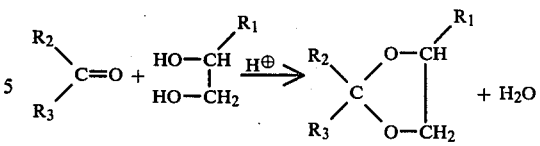

In addition, a relatively large number of the alkyl-substituted 1,3-dioxolanes to be used as perfuming agents according to the invention has been prepared by special methods, as is described for 2,2-dimethyl-4-dodecyl-1,3-dioxolane by R. P. Hanzlik and M. Leinwetter in *J. Org. Chem.*, Vol. 43, 438 (1978); for 4-heptyl-, 4-octyl-, 4-decyl-, and 4-dodecyl-1,3-dioxolane by I. Rosenthal and D. Elad in *J. Org. Chem.*, Vol. 33, 805 (1968); for 4-octyl-1,3-dioxolane by R. Lalende et al. in *Tetrahedron Letters*, 1969, 745; for 2,2-dimethyl-4-pentyl-1,3-dioxolane by S. Raucher in *Tetrahedron Letters*, 1976, 1161; for 2,2-dimethyl-4-undecyl-1,3-dioxolane by H. Nakada in *Agric. Biol. Chem.*, Vol. 41, 1761 (1977); and for 2-methyl-4-hexyl-1,3-dioxolane by E. Tobler in *Helv. Chim. Acta.*, Vol. 52, 408 (1969). However, none of these publications provides any information about the fragrance characteristics or that such alkyl-substituted 1,3-dioxolanes can be used advantageously as perfuming agents in the most widely varying perfuming compositions.

Alkyl-substituted 1,3-dioxolanes that can be used according to the invention are, for example, 4-hexyl-, 4-octyl-, 4-decyl-, 2-methyl-4-hexyl-, 2-methyl-4-octyl-, 2-methyl-4-decyl-, 2-ethyl-4-octyl-, 2-isopropyl-4-decyl-, 2-isopropyl-4-dodecyl-, 2-pentyl-4-hexyl-, 2-heptyl-4-butyl-, 2,2-dimethyl-4-hexyl-, 2,2-dimethyl-4-octyl-, 2-methyl-2-ethyl-4-butyl-, 2-methyl-2-ethyl-4-hexyl-, 2-cyclohexyl-4-butyl-, 2-cyclohex-3-enyl-4-butyl-, 2-cyclooctyl-4-butyl-, 2-α-furyl-4-butyl-, 2-cyclohex-3-enyl-4-hexyl-, 2-phenyl-4-hexyl-, 2-phenyl-4-octyl-, 2-isobutyl-4-butyl-, 2-isobutyl-4-hexyl-, 2-isobutyl-4-octyl-, 2-(2-pentyl)-4-butyl-, or 2-(2-pentyl)-4-hexyl-1,3-dioxolane.

The alkyl-substituted 1,3-dioxolanes to be used according to the invention represent valuable perfuming agents with characteristic, interesting perfume notes. A particular advantage is the fact that they combine readily into novel fragrance nuances.

The alkyl-substituted 1,3-dioxolanes to be used according to the invention can be mixed with other perfumes in various quantity ratios to provide new perfume compositions. Generally, the content of the alkyl-substituted 1,3-dioxolanes in the perfume compositions will range from about 1 to 50 percent by weight, based on the weight of the total composition. Such compositions can serve directly as perfume or also as perfuming agents in cosmetics, such as creams, lotions, toilet waters, aerosols, mouth-care products, toilet soaps, and the like. Also, they may be used to improve the odor of industrial and commercial products such as detergents and cleansing agents, disinfectants, softeners, textile treatment agents, and the like. To perfume the various products, the perfume compositions containing the alkyl-substituted 1,3-dioxolanes to be used according to the invention are added to the products generally in concentrations of from about 0.05 to 2 percent by weight, based on the total weight of the products.

The following examples are intended to illustrate the invention in greater detail and are not to be construed as limiting the invention thereto.

EXAMPLES

Examples 1 TO 27

Several alkyl-substituted 1,3-dioxolanes to be used according to the invention were prepared using a general preparation method. According to this method, 0.1 mol of the respective carbonyl compound, 0.1 mol of the respective 1,2-alkane diol, 0.1 mol of orthoformic acid triethyl ester, and 0.5 gm of p-toluene sulfonic acid were agitated for one hour at room temperature. Then, a mixture of ethyl formate and ethanol was distilled off slowly. The cooled residue was taken up in ether, washed with an aqueous sodium carbonate solution, dried over sodium sulfate, evaporated, and distilled under vacuum.

The compounds prepared and their characteristics are set forth in the following table:

TABLE

| Example | Compound | Perfume Note | Boiling Point (°C.) | Pressure (mbar) | Refractive Index ($n_D^{20}$) |
|---|---|---|---|---|---|
| 1 | 4-Hexyl-1,3-dioxolane | bitter nut note | 42 | 0.02 | 1.4335 |
| 2 | 4-Octyl-1,3-dioxolane | fatty aldehyde note | | | 1.4381 |
| 3 | 4-Decyl-1,3-dioxolane | fresh geranyl acetate note | 90 | 0.02 | 1.4430 |
| 4 | 2-Methyl-4-hexyl-1,3-dioxolane | fruity, cabbage-like | — | — | 1.4292 |
| 5 | 2-Methyl-4-octyl-1,3-dioxolane | lovage note | 69 | 0.02 | 1.4348 |
| 6 | 2-Methyl-4-decyl-1,3-dioxolane | walnut-jasmone note | 80 | 0.02 | 1.4396 |
| 7 | 2-Ethyl-4-octyl-1,3-dioxolane | lovage, walnut note | 78 | 0.02 | 1.4342 |
| 8 | 2-Isopropyl-4-decyl-1,3-dioxolane | sweet St. John's bread note | 135 | 0.65 | 1.4423 |
| 9 | 2-Isopropyl-4-dodecyl-1,3-dioxolane | St. John's bread note | 155 | 0.65 | 1.4462 |
| 10 | 2-Pentyl-4-hexyl-1,3-dioxolane | flowery, green | 75 | 0.02 | 1.4389 |
| 11 | 2-Heptyl-4-butyl-1,3-dioxolane | nut note, sweet | 140 | 20 | 1.4396 |
| 12 | 2,2-Dimethyl-4-hexyl-1,3-dioxolane | jasmone note | 50 | 0.15 | 1.4251 |
| 13 | 2,2-Dimethyl-4-octyl-1,3-dioxolane | fresh laundry note | 122 | 20 | 1.4322 |
| 14 | 2-Methyl-2-ethyl-4-butyl-1,3-dioxolane | fruity, cabbage-like | 73 | 16 | 1.4240 |
| 15 | 2-Methyl-2-ethyl-4-hexyl-1,3-dioxolane | spicy | 105 | 20 | 1.4308 |
| 16 | 2-Cyclohexyl-4-butyl-1,3-dioxolane | fruity | 54 | 0.06 | 1.4602 |
| 17 | 2-Cyclohex-3-enyl-4-butyl-1,3-dioxolane | fruity, raspberry, strawberry note | 70 | 0.03 | 1.4702 |
| 18 | 2-Cyclooctyl-4-butyl-1,3-dioxolane | sweet | 91 | 0.02 | 1.4728 |
| 19 | 2-α-Furyl-4-butyl-1,3-dioxolane | jasmone, mushroom note | 63 | 0.02 | 1.4708 |
| 20 | 2-Cyclohex-3-enyl-4-hexyl-1,3-dioxolane | raspberry, strawberry note | 90 | 0.02 | 1.4699 |
| 21 | 2-Phenyl-4-hexyl-1,3-dioxolane | flowery, sweet, tobacco note | 104 | 0.06 | 1.4952 |
| 22 | 2-Phenyl-4-octyl-1,3-dioxolane | fatty alcohol note | 118 | 0.02 | 1.4920 |
| 23 | 2-Isobutyl-4-butyl-1,3-dioxolane | pineapple note | 96 | 23 | 1.4295 |
| 24 | 2-Isobutyl-4-hexyl-1,3-dioxolane | dry fruity | 125 | 23 | 1.4350 |
| 25 | 2-Isobutyl-4-octyl-1,3-dioxolane | blueberry note | 154 | 21 | 1.4395 |
| 26 | 2-(2-Pentyl)-4-butyl-1,3-dioxolane | sweet | 109 | 21 | 1.4335 |
| 27 | 2-(2-Pentyl)-4-hexyl-1,3-dioxolane | strawberry note | 100 | 7 | 1.4385 |

Several typical perfume compositions containing alkyl-substituted 1,3-dioxolanes are set forth below in Examples 28 and 29. The alkyl-substituted 1,3-dioxolane given in each example could readily be replaced by a similar such compound within the scope of the invention.

Example 28

| Fruit Complex | |
|---|---|
| Component | Amount (parts by weight) |
| 2-Cyclohex-3-enyl-4-butyl-1,3-dioxolane | 300 |
| Phenylethyl alcohol | 130 |
| Benzyl acetate | 100 |
| Linalyl acetate | 50 |
| Citronellol | 50 |
| Lemon oil | 50 |
| Orange oil, sweet | 50 |
| Cyclovertal, 10% | 50 |
| Phenylethyl acetate | 40 |
| Aldehyde $C_{18}$ (nonalactone), 10% | 40 |
| Galaxolide | 30 |
| Aurantesine | 30 |
| Benzyl propionate | 30 |
| Aldehyde $C_{14}$ (undecalactone), 10% | 20 |

-continued

| Fruit Complex | |
|---|---|
| Component | Amount (parts by weight) |
| Phenylisobutyrate | 20 |
| Cyclamen aldehyde | 10 |
| | 1000 |

Example 29

| Jasmine Complex | |
|---|---|
| Component | Amount (parts by weight) |
| 2,2-Dimethyl-4-hexyl-1,3-dioxolane | 100 |
| Linalool | 350 |
| Benzyl acetate | 100 |
| Lyral | 100 |
| Dimethylbenzylcarbinyl acetate | 50 |
| Benzylsalicylate | 50 |
| Ethyl linalool | 50 |
| Benzyl alcohol | 40 |
| Ylang-Ylang oil | 40 |
| Benzylphenyl acetate | 20 |
| Citronellol | 20 |
| Benzylbenzoate | 20 |
| Cyclamen aldehyde | 15 |
| α-Amylcinnamaldehyde | 15 |
| Methylnaphthyl ketone | 10 |
| Nerol | 10 |
| Methyl eugenol | 6 |
| Indoflor | 1 |
| Hexenylbenzoate | 1 |
| Methylheptenone, 20% | 1 |
| Decanal, 10% | 1 |
| | 1000 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A perfumery composition consisting essentially of from about 1 to 50 percent by weight of at least one alkyl-substituted 1,3-dioxolane of the formula

wherein $R_1$ represents an alkyl of from 4 to 12 carbon atoms; $R_2$ represents a cycloalkyl or cycloalkenyl of from 5 to 8 carbon atoms, an optionally alkyl-substituted aryl, or a furyl group; and $R_3$ represents hydrogen or an alkyl of from 1 to 3 carbon atoms, and the remainder of customary constituents of perfumery compositions.

2. The perfumery composition of claim 1, wherein in the compound of formula I $R_1$ is a butyl, hexyl, octyl, decyl, or dodecyl group;
$R_2$ is a cyclohexyl, cyclohexenyl, cyclooctyl, phenyl, lower alkyl-substituted phenyl, naphthyl, lower alkyl-substituted naphthyl, or furyl group; and
$R_3$ is hydrogen or a methyl, ethyl, propyl, or isopropyl group.

3. The method of imparting a pleasant odor to a product comprising the step of adding to said product a sufficient amount of the perfumery composition of claim 1 to provide the desired degree of odor.

4. The method of claim 3 wherein the amount of perfumery composition added consists of from about 0.05 to 5 percent by weight, based on the weight of the total product.

5. The perfume composition of claim 1, wherein $R_2$ is cycloalkyl or cycloalkenyl of from 5 to 8 carbon atoms.

6. The perfume composition of claim 1, wherein $R_2$ is an optionally alkyl-substituted aryl.

7. The perfume composition of claim 1, wherein $R_2$ is a furyl group.

8. A perfumery composition consisting essentially of from about 1 to 50 percent by weight of at least one alkyl-substituted, 1,3-dioxolane selected from the group consisting of 2-ethyl-4-octyl-1,3-dioxolane, 2-isopropyl-4-decyl-1,3-dioxolane, 2-isopropyl-4-dodecyl-1,3-dioxolane, 2-pentyl-4-hexyl-1,3-dioxolane, 2-heptyl-4-butyl-1,3-dioxolane, 2-methyl-2-ethyl-4-butyl-1,3-dioxolane, 2-methyl-2-ethyl-4-hexyl-1,3-dioxolane, and 2-isobutyl-4-butyl-1,3-dioxolane, and the remainder of the customary constituents of perfumery compositions.

9. The method of imparting a pleasant odor to a product comprising the step of adding to said product a sufficient amount of the perfumery composition of claim 8 to provide the desired degree of odor.

10. The method of claim 9 wherein the amount of perfumery composition added consists of from about 0.05 to 5 percent by weight, based on the weight of the total product.

11. The perfume composition of claim 8, wherein the alkyl-substituted 1,3-dioxolane is 2-ethyl-4-octyl-1,3-dioxolane.

12. The perfume composition of claim 8, wherein the alkyl-substituted 1,3-dioxolane is 2-isopropyl-4-decyl-1,3-dioxolane.

13. The perfume composition of claim 8, wherein the alkyl-substituted 1,3-dioxolane is 2-isopropyl-4-dodecyl-1,3-dioxolane.

14. The perfume composition of claim 8, wherein the alkyl-substituted 1,3-dioxolane is 2-pentyl-4-hexyl-1,3-dioxolane.

15. The perfume composition of claim 8, wherein the alkyl-substituted 1,3-dioxolane is 2-heptyl-4-butyl-1,3-dioxolane.

16. The perfume composition of claim 8, wherein the alkyl-substituted 1,3-dioxolane is 2-methyl-2-ethyl-4-butyl-1,3-dioxolane.

17. The perfume composition of claim 8, wherein the alkyl-substituted 1,3-dioxolane is 2-methyl-2-ethyl-4-hexyl-1,3-dioxolane.

18. The perfume composition of claim 1, wherein the alkyl-substituted 1,3-dioxolane is 2-cyclohexyl-4-butyl-1,3-dioxolane.

19. The perfume composition of claim 1, wherein the alkyl-substituted 1,3-dioxolane is 2-cyclohex-3-enyl-4-butyl-1,3-dioxolane.

20. The perfume composition of claim 1, wherein the alkyl-substituted 1,3-dioxolane is 2-cyclooctyl-4-butyl-1,3-dioxolane.

21. The perfume composition of claim 1, wherein the alkyl-substituted 1,3-dioxolane is 2-α-furyl-4-butyl-1,3-dioxolane.

22. The perfume composition of claim 1, wherein the alkyl-substituted 1,3-dioxolane is 2-cyclohex-3-enyl-4-hexyl-1,3-dioxolane.

23. The perfume composition of claim 1, wherein the alkyl-substituted 1,3-dioxolane is 2-phenyl-4-hexyl-1,3-dioxolane.

24. The perfume composition of claim 1, wherein the alkyl-substituted 1,3-dioxolane is 2-phenyl-4-octyl-1,3-dioxolane.

25. The perfume composition of claim 8, wherein the alkyl-substituted 1,3-dioxolane is 2-isobutyl-4-butyl-1,3-dioxolane.

26. The perfume composition of claim 1, wherein the alkyl-substituted 1,3-dioxolane is 2-isobutyl-4-hexyl-1,3-dioxolane.

27. The perfume composition of claim 1, wherein the alkyl-substituted 1,3-dioxolane is 2-isobutyl-4-octyl-1,3-dioxolane.

28. The perfume composition of claim 1, wherein the alkyl-substituted 1,3-dioxolane is 2-(2-pentyl)-4-butyl-1,3-dioxolane.

29. The perfume composition of claim 1, wherein the alkyl-substituted 1,3-dioxolane is 2-(2-pentyl)-4-hexyl-1,3-dioxolane.

* * * * *